(12) United States Patent
Ida et al.

(10) Patent No.: US 9,551,693 B2
(45) Date of Patent: Jan. 24, 2017

(54) PHOTOACOUSTIC WAVE MEASUREMENT DEVICE, METHOD, PROGRAM, AND RECORDING MEDIUM

(71) Applicant: ADVANTEST CORPORATION, Tokyo (JP)

(72) Inventors: Taiichiro Ida, Gunma (JP); Yasushi Kawaguchi, Saitama (JP)

(73) Assignee: ADVANTEST CORPORATION, Tokyo (JP)

( * ) Notice: Subject to any disclaimer, the term of this patent is extended or adjusted under 35 U.S.C. 154(b) by 162 days.

(21) Appl. No.: 14/383,275

(22) PCT Filed: May 2, 2013

(86) PCT No.: PCT/JP2013/063229
§ 371 (c)(1),
(2) Date: Sep. 5, 2014

(87) PCT Pub. No.: WO2013/183399
PCT Pub. Date: Dec. 12, 2013

(65) Prior Publication Data
US 2015/0047433 A1 Feb. 19, 2015

(30) Foreign Application Priority Data

Jun. 4, 2012 (JP) .................................. 2012-127103

(51) Int. Cl.
*G01N 29/34* (2006.01)
*G01N 29/44* (2006.01)
(Continued)

(52) U.S. Cl.
CPC ............. *G01N 29/38* (2013.01); *A61B 5/0095* (2013.01); *A61B 8/429* (2013.01);
(Continued)

(58) Field of Classification Search
CPC ..... A61B 5/0095; A61B 5/7203; A61B 8/429; A61B 8/5269; A61B 8/4281; G01N 29/2418; G01N 21/1702; G01N 29/343; G01N 29/38; G01N 29/44; G01N 2021/1708
(Continued)

(56) References Cited

U.S. PATENT DOCUMENTS 5,083,869 A * 1/1992 Nakata ............... G01N 21/1702
356/432
5,136,172 A * 8/1992 Nakata ............... G01N 21/1702
250/559.39
(Continued)

FOREIGN PATENT DOCUMENTS

JP 2011-055902 3/2011
JP 2011-183149 9/2011
(Continued)

OTHER PUBLICATIONS

Search Report issued by E.P.O. patent office in E.P.O. Patent Application No. 13800997.2, dated Mar. 3, 2016.
(Continued)

*Primary Examiner* — J M Saint Surin
(74) *Attorney, Agent, or Firm* — Greenblum & Bernstein, P.L.C.

(57) ABSTRACT

A photoacoustic wave measurement device includes: (a) a pulsed-light outputter that outputs a pulsed light; (b) an arrangement member disposed between a pulsed-light output end of the pulsed-light outputter and a measurement object, the arrangement member being adapted to allow the pulsed light to pass therethrough; and (c) a photoacoustic wave detector that receives a photoacoustic wave generated by the measurement object by the pulsed light and that converts the photoacoustic wave into an electric signal, the photoacoustic wave measurement device being adapted to
(Continued)

receive the electric signal from a photoacoustic wave sensor in which the photoacoustic wave detector is farther from the measurement object than the pulsed-light output end. The photoacoustic wave measurement device further includes: an electric signal recording section that receives and records the electric signal from the photoacoustic wave sensor; a noise timing estimation section that estimates timing of occurrence of noise in the electric signal, from a thickness of the arrangement member; and a noise removal section that removes the electric signal at the timing estimated, from contents recorded by the electric signal recording section.

7 Claims, 4 Drawing Sheets

(51) Int. Cl.
    *G01N 29/24*         (2006.01)
    *G01N 21/17*         (2006.01)
    *A61B 5/00*          (2006.01)
    *A61B 8/00*          (2006.01)
    *G01N 29/38*         (2006.01)
    *A61B 8/08*          (2006.01)

(52) U.S. Cl.
    CPC ..... *G01N 21/1702* (2013.01); *G01N 29/2418* (2013.01); *G01N 29/343* (2013.01); *G01N 29/44* (2013.01); *A61B 8/4281* (2013.01); *A61B 8/5269* (2013.01); *G01N 2021/1708* (2013.01)

(58) Field of Classification Search
    USPC ......................................................... 73/645
    See application file for complete search history.

(56) References Cited

U.S. PATENT DOCUMENTS

| | | | |
|---|---|---|---|
| 6,108,096 A * | 8/2000 | Ushio | G01N 21/1702 356/432 |
| 2007/0015978 A1 | 1/2007 | Kanayama et al. | |
| 2010/0053618 A1 | 3/2010 | Nakajima et al. | |
| 2011/0112391 A1 | 5/2011 | Nishihara et al. | |
| 2011/0194380 A1 | 8/2011 | Fukutani | |
| 2012/0130222 A1* | 5/2012 | Kobayashi | A61B 5/0095 600/407 |
| 2012/0133941 A1 | 5/2012 | Nakajima et al. | |
| 2012/0325006 A1 | 12/2012 | Suzuki | |
| 2013/0121106 A1 | 5/2013 | Nishihara | |
| 2013/0123604 A1 | 5/2013 | Oyama | |
| 2013/0131487 A1* | 5/2013 | Nagao | A61B 5/0095 600/407 |
| 2014/0307259 A1 | 10/2014 | Ida | |
| 2014/0309515 A1 | 10/2014 | Ida | |
| 2014/0309516 A1 | 10/2014 | Ida | |
| 2015/0075288 A1* | 3/2015 | Ida | A61B 5/0095 73/655 |

FOREIGN PATENT DOCUMENTS

| | | |
|---|---|---|
| JP | 2011-229660 | 11/2011 |
| JP | 2012-24460 | 2/2012 |
| JP | 2012-29715 | 2/2012 |
| JP | 2012-86037 | 5/2012 |

OTHER PUBLICATIONS

U.S. Appl. No. 14/397,939 to Taiichiro Ida, filed Oct. 30, 2014.
U.S. Appl. No. 14/382,596 to Taiichiro Ida, filed Sep. 3, 2014.
U.S. Appl. No. 14/383,292 to Yasushi Kawaguchi et al., filed Sep. 5, 2014.
Search report from International Bureau of WIPO, Application No. PCT/JP2013/063229, mail date is Jun. 4, 2013.

* cited by examiner

Preferred Embodiment

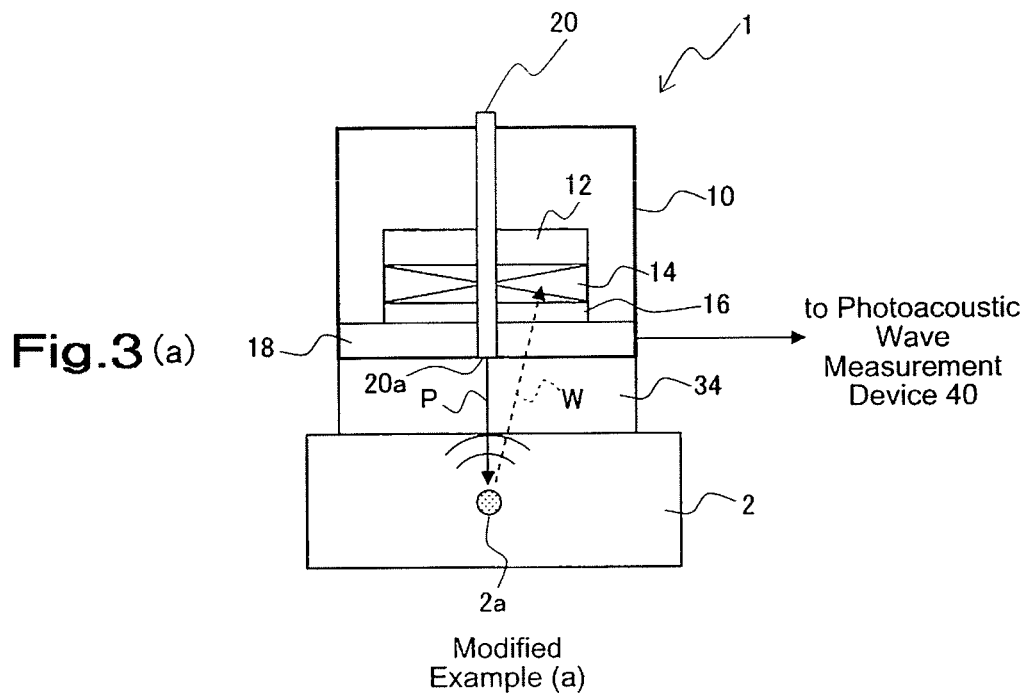
Fig.3 (a)  Modified Example (a)
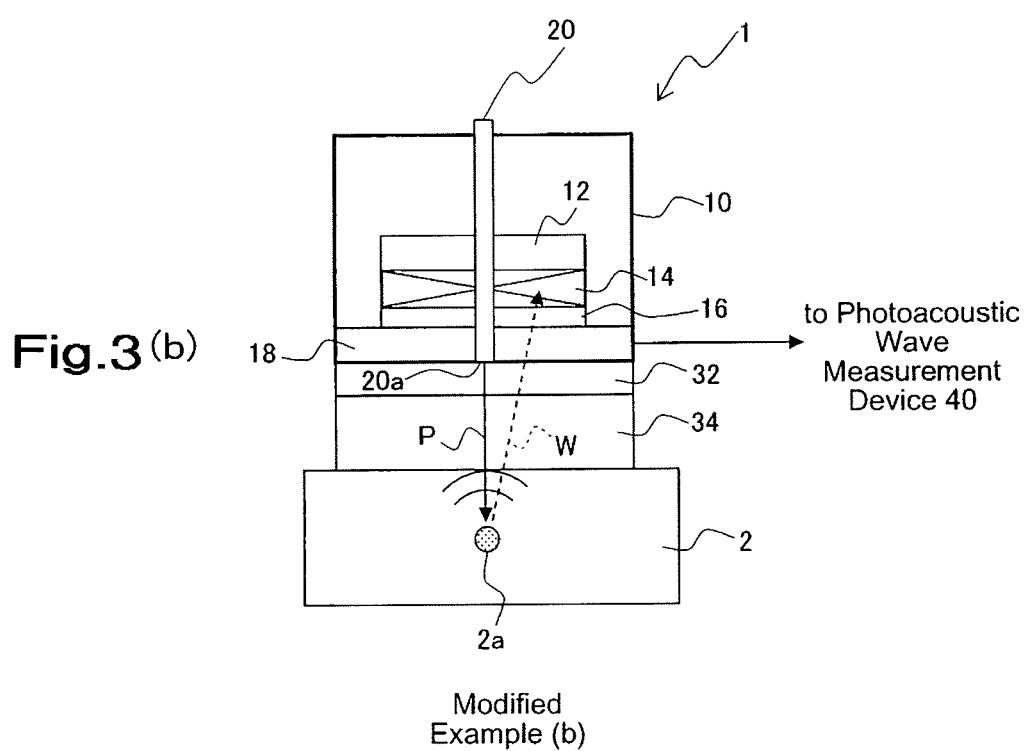
Fig.3 (b)  Modified Example (b)

PHOTOACOUSTIC WAVE MEASUREMENT DEVICE, METHOD, PROGRAM, AND RECORDING MEDIUM

FIELD OF THE INVENTION

The present invention relates to photoacoustic sensors.

BACKGROUND ART

Photoacoustic sensors are conventionally known to measure a photoacoustic signal generated by irradiating an object to be measured (e.g. biological object) with pulsed light (see, for example, Patent Document 1 (Japanese Unexamined Patent Publication No. 2011-229660)).

SUMMARY OF THE INVENTION

Such a photoacoustic signal obtained by the photoacoustic sensor, however, might have noise superimposed thereon.

Accordingly, it is an object of the present invention to reduce noise to be superimposed on the photoacoustic signal obtained by the photoacoustic wave measurement device.

According to the present invention, a photoacoustic wave measurement device includes: (a) a pulsed-light outputter that outputs a pulsed light; (b) an arrangement member disposed between a pulsed-light output end of the pulsed-light outputter and a measurement object, the arrangement member being adapted to allow the pulsed light to pass therethrough; and (c) a photoacoustic wave detector that receives a photoacoustic wave generated by the measurement object by the pulsed light and that converts the photoacoustic wave into an electric signal, the photoacoustic wave measurement device being adapted to receive the electric signal from a photoacoustic wave sensor in which the photoacoustic wave detector is farther from the measurement object than the pulsed-light output end, wherein the photoacoustic wave measurement device further includes: an electric signal recording section that receives and records the electric signal from the photoacoustic wave sensor; a noise timing estimation section that estimates timing of occurrence of noise in the electric signal, from a thickness of the arrangement member; and a noise removal section that removes the electric signal at the timing estimated, from contents recorded by the electric signal recording section.

According to the thus constructed photoacoustic wave measurement device, a photoacoustic wave measurement device including: (a) a pulsed-light outputter that outputs a pulsed light; (b) an arrangement member disposed between a pulsed-light output end of the pulsed-light outputter and a measurement object, the arrangement member being adapted to allow the pulsed light to pass therethrough; and (c) a photoacoustic wave detector that receives a photoacoustic wave generated by the measurement object by the pulsed light and that converts the photoacoustic wave into an electric signal, the photoacoustic wave measurement device being adapted to receive the electric signal from a photoacoustic wave sensor in which the photoacoustic wave detector is farther from the measurement object than the pulsed-light output end, can be provided. An electric signal recording section receives and records the electric signal from the photoacoustic wave sensor. A noise timing estimation section estimates timing of occurrence of noise in the electric signal, from a thickness of the arrangement member. A noise removal section removes the electric signal at the timing estimated, from contents recorded by the electric signal recording section.

According to the photoacoustic wave measurement device of the present invention, the arrangement member may have such a sufficient thickness that noise to be detected by the photoacoustic wave detector after a start time of detection of the photoacoustic wave starts to be detected after an end time of the detection of the photoacoustic wave.

According to the photoacoustic wave measurement device of the present invention, the pulsed-light outputter may be an optical fiber.

According to the photoacoustic wave measurement device of the present invention, the photoacoustic wave detector may be a piezoelectric element.

The present invention is a method of measuring a photoacoustic wave by using a photoacoustic wave measurement device including: (a) a pulsed-light outputter that outputs a pulsed light; (b) an arrangement member disposed between a pulsed-light output end of the pulsed-light outputter and a measurement object, the arrangement member being adapted to allow the pulsed light to pass therethrough; and (c) a photoacoustic wave detector that receives a photoacoustic wave generated by the measurement object by the pulsed light and that converts the photoacoustic wave into an electric signal, the photoacoustic wave measurement device being adapted to receive the electric signal from a photoacoustic wave sensor in which the photoacoustic wave detector is farther from the measurement object than the pulsed-light output end, the method including: an electric signal recording step that receives and records the electric signal from the photoacoustic wave sensor; a noise timing estimation step that estimates timing of occurrence of noise in the electric signal, from a thickness of the arrangement member; and a noise removal step that removes the electric signal at the timing estimated, from contents recorded by the electric signal recording step.

The present invention is a program of instructions for execution by a computer to perform a process of measuring a photoacoustic wave by using a photoacoustic wave measurement device including: (a) a pulsed-light outputter that outputs a pulsed light; (b) an arrangement member disposed between a pulsed-light output end of the pulsed-light outputter and a measurement object, the arrangement member being adapted to allow the pulsed light to pass therethrough; and (c) a photoacoustic wave detector that receives a photoacoustic wave generated by the measurement object by the pulsed light and that converts the photoacoustic wave into an electric signal, the photoacoustic wave measurement device being adapted to receive the electric signal from a photoacoustic wave sensor in which the photoacoustic wave detector is farther from the measurement object than the pulsed-light output end, the process including: an electric signal recording step that receives and records the electric signal from the photoacoustic wave sensor; a noise timing estimation step that estimates timing of occurrence of noise in the electric signal, from a thickness of the arrangement member; and a noise removal step that removes the electric signal at the timing estimated, from contents recorded by the electric signal recording step.

The present invention is a computer-readable medium having a program of instructions for execution by a computer to perform a process of measuring a photoacoustic wave by using a photoacoustic wave measurement device including: (a) a pulsed-light outputter that outputs a pulsed light; (b) an arrangement member disposed between a pulsed-light output end of the pulsed-light outputter and a measurement object, the arrangement member being adapted to allow the pulsed light to pass therethrough; and (c) a photoacoustic wave detector that receives a photoacoustic wave generated by the measurement object by the pulsed light and that converts the photoacoustic wave into an electric signal, the photoacoustic wave measurement device being adapted to receive the electric signal from a photoacoustic wave sensor in which the photoacoustic wave detector is farther from the measurement object than the pulsed-light output end, the process including: an electric signal recording step that receives and records the electric signal from the photoacoustic wave sensor; a noise timing estimation step that estimates timing of occurrence of noise in the electric signal, from a thickness of the arrangement member; and a noise removal step that removes the electric signal at the timing estimated, from contents recorded by the electric signal recording step.

BRIEF DESCRIPTION OF DRAWINGS

FIG. 3(a) shows a cross-sectional view of another photoacoustic wave sensor 1 in a modified example (a), and FIG. 3(b) shows a cross-sectional view of a further photoacoustic wave sensor 1 in another modified example (b)

MODES FOR CARRYING OUT THE INVENTION

A description will now be given of an embodiment of the present invention referring to drawings.

Figure 1:
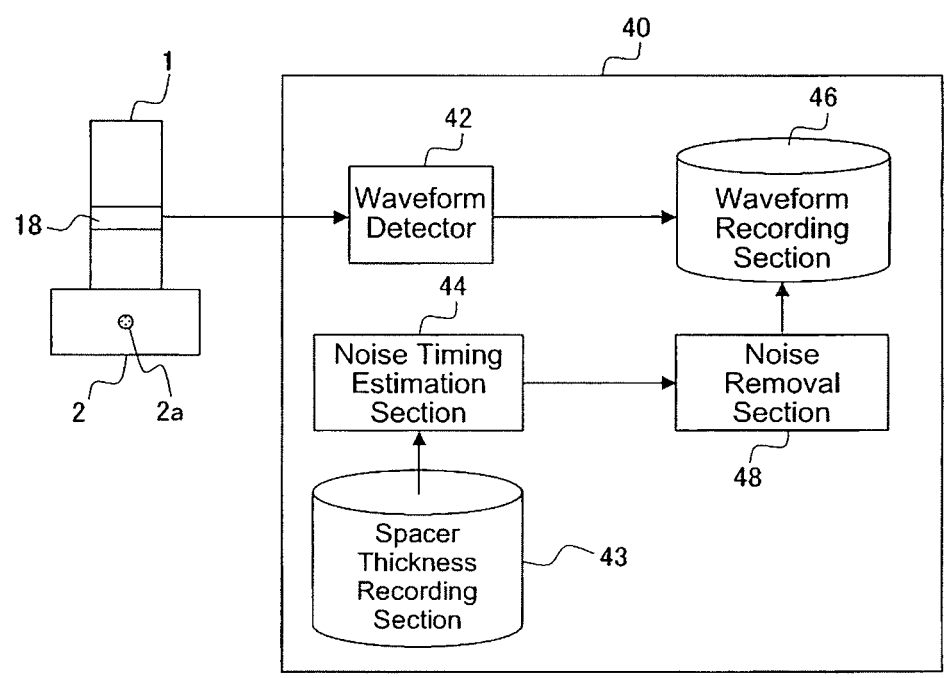
FIG. 1 is a functional block diagram showing the configuration of a photoacoustic wave measurement device 40 according to one embodiment of the present invention.

FIG. 1 is a functional block diagram showing the configuration of a photoacoustic wave measurement device 40 according to one embodiment of the present invention. The photoacoustic wave measurement device 40 receives an electric signal from a photoacoustic wave sensor 1. The photoacoustic wave measurement device 40 includes a waveform detector 42, a spacer thickness recording section 43, a noise timing estimation section 44, a waveform recording section (i.e. electric signal recording section) 46, and a noise removal section 48.

Figure 2:
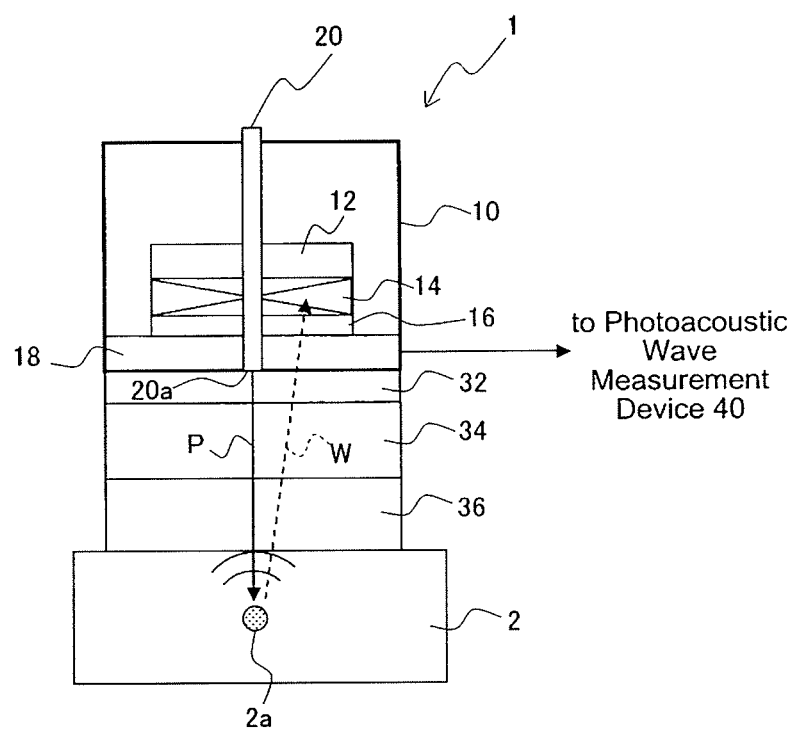
FIG. 2 is a cross-sectional view of the photoacoustic wave sensor 1 according to the one embodiment of the present invention.

FIG. 2 is a cross-sectional view of the photoacoustic wave sensor 1 according to the one embodiment of the present invention. The photoacoustic wave sensor 1 includes a case 10, a backing member 12, a piezoelectric element (i.e. photoacoustic wave detector) 14, an electrode 16, a spacer 18, an optical fiber (i.e. pulsed-light outputter) 20, and external spacers (i.e. arrangement members) 32, 34, and 36.

The photoacoustic wave sensor 1 shown in FIG. 2 is more preferable than the photoacoustic wave sensor 1 shown in FIG. 3. This is because noise B (see FIG. 4) is not superimposed on a photoacoustic wave W (see FIG. 4) as described later.

The case 10 is a case for accommodating therein the backing member 12, the piezoelectric element 14, the electrode 16, and the spacer 18. The spacer 18 is in contact with the bottom surface of the case 10, and the electrode 16 is mounted on the spacer 18. The piezoelectric element 14 is mounted on the electrode 16, and the backing member 12 is mounted on the piezoelectric element 14.

The backing member 12 serves as a backing material made of epoxy resin. The piezoelectric element (i.e. photoacoustic wave detector) 14 receives a pressure caused by compression waves or the like and converts the pressure into a voltage. The electrode 16 receives the voltage from the piezoelectric element 14 and supplies the voltage to the photoacoustic wave measurement device 40. The electrode 16 is, for example, a gold electrode. The spacer 18 allows the compression waves to pass therethrough. The spacer 18 is a transparent spacer, for example, made of polystyrene.

The optical fiber (i.e. pulsed light outputter) 20 outputs a pulsed light P from a pulsed-light output end 20a. The optical fiber 20 is connected to a pulse light source (not shown) outside the photoacoustic wave sensor 1. The optical fiber 20 penetrates through the case 10, the backing member 12, the piezoelectric element 14, the electrode 16, and the spacer 18.

The external spacers (i.e. arrangement members) 32, 34, and 36 are disposed between the pulsed-light output end 20a and a measurement object 2 so as to allow the pulsed light P to pass therethrough. The external spacer 32 is in contact with the case 10 and the pulsed-light output end 20a. The external spacer 36 is in contact with the measurement object 2. The external spacer 34 is disposed between the external spacer 32 and the external spacer 36.

The external spacer (i.e. arrangement member) 32 is a spacer, for example, made of white polycarbonate of 1.5 mm in thickness. Each of the external spacers (i.e. arrangement members) 34 and 36 is a transparent spacer made of polystyrene of 4.0 mm in thickness. Note that the external spacers 32, 34, and 36 may be integrally formed together.

The measurement object 2 is, for example, a finger cushion of a human being. The measurement object 2 includes a blood vessel 2a. When receiving the pulsed light P, the blood vessel 2a generates a photoacoustic wave W. The piezoelectric element 14 receives the photoacoustic wave W and converts the wave W into an electric signal (for example, in the form of a voltage). The piezoelectric element 14 is farther from the measurement object 2 than the pulsed-light output end 20a.

FIG. 3(a) shows a cross-sectional view of another photoacoustic wave sensor 1 in a modified example (a), and FIG. 3(b) shows a cross-sectional view of a further photoacoustic wave sensor 1 in another modified example (b).

The modified example (a) is one obtained by removing the external spacers 32 and 36 from the photoacoustic wave sensor 1 shown in FIG. 2. The modified example (b) is one obtained by removing the external spacer 36 from the photoacoustic wave sensor 1 shown in FIG. 2.

Returning to FIG. 1, the configuration of the photoacoustic wave measurement device 40 will be described below.

The waveform detector 42 receives an electric signal (for example, in the form of a voltage) from the electrode 16 and detects its waveform, and sends the detected waveform to the waveform recording section 46.

The spacer thickness recording section 43 records the thickness of the external spacer.

The noise timing estimation section 44 estimates timing of occurrence of noise in the electric signal (for example, in the form of the voltage), from the thickness of the external spacer (i.e. arrangement member) recorded by the spacer thickness recording portion 43.

Figure 4:
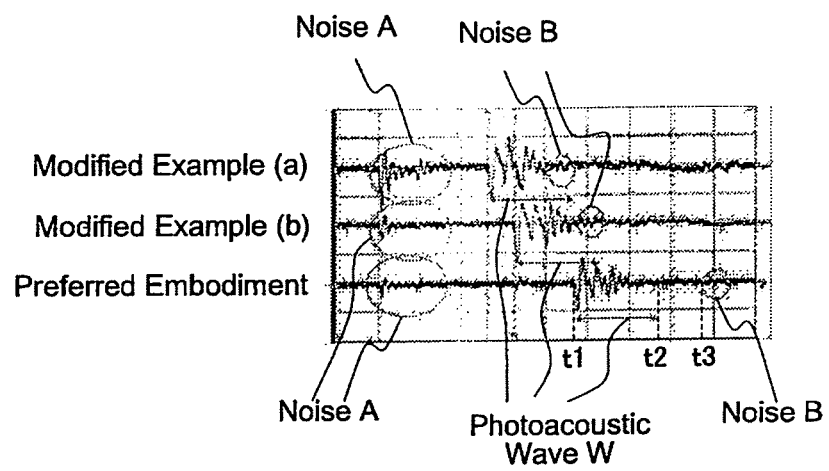
FIG. 4 shows a graph of waveforms detected by the photoacoustic wave sensors 1 in the modified examples (a) and (b) (see FIGS. 3(a) and (b)), and by the photoacoustic wave sensor 1 in the one preferred embodiment of the present invention (see FIG. 2).

The waveform recording section (i.e. electric signal recording section) 46 receives an electric signal from the photoacoustic wave sensor 1 via the waveform detector 42, and records the electric signal therein (see FIG. 4).

The noise removal section 48 removes the electric signal at the timing estimated, from the contents recorded by the waveform recording section (i.e. electric signal recording section) 46.

Next, the operation of the embodiment in the present invention will be described below.

First, an external pulsed light source (not shown) emits a pulsed light P, and the pulsed light P passes through the optical fiber 20. Then, the pulsed light P is output from the pulsed-light output end 20a. The pulsed light P is applied to the measurement object 2 through the external spacers 32, 34, and 36.

The pulsed light P reaches the blood vessel 2a of the measurement object 2. At this time, the blood vessel 2a absorbs the pulsed light P and is warmed and is then adiabatically expanded. Thus, the compression waves (i.e. photoacoustic waves W) are output from the blood vessel 2a.

The photoacoustic waves W reach the piezoelectric element 14 through the measurement object 2, the external spacers 36, 34, and 32, the spacer 18, and the electrode 16. The piezoelectric element 14 converts the pressure produced by the photoacoustic wave W into an electric signal (for example, in the form of a voltage). The voltage is taken out to the outside via the electrode 16, and then fed to the waveform detector 42 of the photoacoustic wave measurement device 40.

FIG. 4 shows a graph of waveforms detected by the photoacoustic wave sensors 1 in the modified examples (a) and (b) (see FIGS. 3(a) and (b)), and by the photoacoustic wave sensor 1 in the one preferred embodiment of the present invention (see FIG. 2). Such detected waveforms are obtained by the waveform detector 42 and fed to the waveform recording section 46.

Each of the detected waveforms in the modified examples (a) and (b) and the one preferred embodiment of the present invention includes noise A, photoacoustic wave W, and noise B.

The photoacoustic wave W is a photoacoustic wave generated from the blood vessel 2a of the measurement object 2. The photoacoustic wave has a waveform which is to be detected. During a period of time indicated by a bidirectional arrow, the photoacoustic wave W is detected.

The noise A is noise detected by the piezoelectric element 14 before a time t1 when the photoacoustic wave W starts to be detected. In the embodiment of the present invention as well as the modified examples (a) and (b), the noise A is not superimposed on the photoacoustic wave W.

The noise B is noise detected by the piezoelectric element 14 after the time t1 when the photoacoustic wave W starts to be detected. In the modified examples (a) and (b), the noise B is superimposed on the photoacoustic wave W due to insufficient thickness of the external spacer.

In the preferred embodiment of the present invention, however, the noise B is not superimposed on the photoacoustic wave W. That is, in the preferred embodiment of the present invention, a time t3 when the noise B starts to be detected comes after a time t2 of the end of detecting the photoacoustic wave W because of a sufficient thickness of the external spacers 32, 34, and 36.

The thicknesses of the external spacers in respective cases are as follows: (the thickness of the external spacer in the modified example (a))<(the thickness of the external spacer in the modified example (b))<(the thickness of the external spacer in the preferred embodiment of the present invention). As the thickness of the external spacer is increased, the time required for the photoacoustic wave W to reach the piezoelectric element 14 becomes longer. As a result, the detection start time of the photoacoustic wave W in the modified example (b) is delayed more than that in the modified example (a), whereas the detection start time of the photoacoustic wave W in the preferred embodiment of the present invention is delayed more than that in the modified example (b).

Further, the time when the noise B starts to be detected is also delayed more as the thickness of the external spacer is increased. However, it has been newly found from the detected waveforms shown in FIG. 4 that the delay of the detection start time of the noise B due to the increase in thickness of the external spacer is much larger than the delay of the detection start time of the photoacoustic wave W.

This is supposed to be because the photoacoustic wave generated in the vicinity of the pulsed-light output end 20a is reflected by a boundary surface between the external spacer 36 and the measurement object 2, and then reaches the piezoelectric element 14 to cause the noise B. In this case, the detection start time of the noise B is delayed only by a time that requires the photoacoustic wave W to travel about twice as long as the thickness of the external spacer. Thus, the detection start time t3 of the noise B is delayed only by about a time determined by the formula of (external spacer thickness)/(speed of photoacoustic wave W) with respect to the detection start time t1 of the photoacoustic wave W.

By use of the above-mentioned principle, the noise timing estimation section 44 estimates timing of occurrence of the noise B in the electric signal. Specifically, the noise timing estimation section 44 reads a thickness of the external spacers from the spacer thickness recording section 43, determines a value of t3−t1 by dividing the thickness of the external spacers by the speed of the photoacoustic wave W, and then sends data on the value t3−t1 determined to the noise removal section 48.

Additionally, since the photoacoustic wave W is larger in size than the noise B, the time when the waveform of the photoacoustic wave W exceeds a predetermined threshold is regarded as the detection start time t1 of the photoacoustic wave W. In this way, the time t1 can be determined. The noise removal section 48 determines the time t3 by adding the value of t3-t1 fed from the noise timing estimation section 44 to the time t1 thus-obtained, and then deletes a waveform produced after the time t3 from the contents recorded in the waveform recording section (i.e. electric signal recording section) 46.

When the photoacoustic wave W and the noise B are not superimposed on each other, like the preferred embodiment of the present invention, only the noise B can be deleted, which is preferable. However, even though the photoacoustic wave W and the noise B are superimposed on each other as shown in the modified examples (a) and (b), the waveform produced after the time t3 may be removed from the contents recorded in the waveform recording section 46 by the noise removal section 48 if the photoacoustic wave W is allowed to be slightly lost. Although in this case, the photoacoustic wave W is slightly removed, the noise B can also be removed.

In the photoacoustic wave measurement device 40 in the embodiment of the present invention, the time (t3−t1) can be determined in the form of (external spacer thickness)/(speed of photoacoustic wave W) by the noise timing estimation section 44. In this way, the embodiment of the present invention can delete the waveform produced after the time t3, which is a time after the elapse of the period of time (t3−t1) following the detection start time t1 of the photoacoustic wave W, from the contents recorded in the waveform recording section (i.e. electric signal recording section) 46 to thereby remove the noise B.

The embodiments described above can be implemented in the following way. A computer with a CPU, a hard disk, and a media (floppy (trademark) disk, CD-ROM, etc.) reader is adapted to read media that store therein programs for achieving the above-mentioned components, for example, the waveform detector 42, the spacer thickness recording section 43, the noise timing estimation section 44, the waveform recording section 46, and the noise removal section 48. Then, the media read are installed in the hard disk. Even this method can achieve the above-mentioned functions.

The invention claimed is:

1. A photoacoustic wave measurement device comprising:
   a pulsed-light outputter that outputs a pulsed light;
   an arrangement spacer disposed between a pulsed-light output end of the pulsed-light outputter and a measurement object, the arrangement spacer being adapted to allow the pulsed light to pass therethrough;
   a photoacoustic wave detector that receives a photoacoustic wave generated by the measurement object by the pulsed light and that converts the photoacoustic wave into an electric signal, the photoacoustic wave measurement device being configured to receive the electric signal from a photoacoustic wave sensor in which the photoacoustic wave detector is farther from the measurement object than the pulsed-light output end;
   an electric signal recorder that receives and records the electric signal from the photoacoustic wave sensor;
   a noise timing estimator that estimates timing of occurrence of noise in the electric signal, from a thickness of the arrangement spacer; and
   a noise remover that removes the electric signal at the timing estimated, from contents recorded by the electric signal recorder.

2. The photoacoustic wave measurement device according to claim 1, wherein the arrangement spacer has such a sufficient thickness that noise to be detected by the photoacoustic wave detector after a start time of detection of the photoacoustic wave starts to be detected after an end time of the detection of the photoacoustic wave.

3. The photoacoustic wave measurement device according to claim 1, wherein the pulsed-light outputter is an optical fiber.

4. The photoacoustic wave measurement device according to claim 1, wherein the photoacoustic wave detector is a piezoelectric element.

5. A method of measuring a photoacoustic wave by using a photoacoustic wave measurement device including: (a) a pulsed-light outputter that outputs a pulsed light; (b) an arrangement spacer disposed between a pulsed-light output end of the pulsed-light outputter and a measurement object, the arrangement spacer being adapted to allow the pulsed light to pass therethrough; and (c) a photoacoustic wave detector that receives a photoacoustic wave generated by the measurement object by the pulsed light and that converts the photoacoustic wave into an electric signal, the photoacoustic wave measurement device being configured to receive the electric signal from a photoacoustic wave sensor in which the photoacoustic wave detector is farther from the measurement object than the pulsed-light output end, said method comprising:
   receiving and recording the electric signal from the photoacoustic wave sensor;
   estimating timing of occurrence of noise in the electric signal, from a thickness of the arrangement spacer; and
   removing the electric signal at the timing estimated, from contents recorded by the receiving and recording of the electric signal.

6. A program of instructions stored on a non-transitory computer-readable medium for execution by a computer to perform a process of measuring a photoacoustic wave by using a photoacoustic wave measurement device including:
   (a) a pulsed-light outputter that outputs a pulsed light;
   (b) an arrangement spacer disposed between a pulsed-light output end of the pulsed-light outputter and a measurement object, the arrangement spacer being adapted to allow the pulsed light to pass therethrough; and
   (c) a photoacoustic wave detector that receives a photoacoustic wave generated by the measurement object by the pulsed light and that converts the photoacoustic wave into an electric signal, the photoacoustic wave measurement device being configured to receive the electric signal from a photoacoustic wave sensor in which the photoacoustic wave detector is farther from the measurement object than the pulsed-light output end, said process comprising:
   receiving and recording the electric signal from the photoacoustic wave sensor;
   estimating timing of occurrence of noise in the electric signal, from a thickness of the arrangement spacer; and
   removing the electric signal at the timing estimated, from contents recorded by the receiving and recording of the electric signal.

7. A non-transitory computer-readable medium having a program of instructions for execution by a computer to perform a process of measuring a photoacoustic wave by using a photoacoustic wave measurement device including: (a) a pulsed-light outputter that outputs a pulsed light; (b) an arrangement spacer disposed between a pulsed-light output end of the pulsed-light outputter and a measurement object, the arrangement spacer being adapted to allow the pulsed light to pass therethrough; and (c) a photoacoustic wave detector that receives a photoacoustic wave generated by the measurement object by the pulsed light and that converts the photoacoustic wave into an electric signal, the photoacoustic wave measurement device being configured to receive the electric signal from a photoacoustic wave sensor in which the photoacoustic wave detector is farther from the measurement object than the pulsed-light output end, said process comprising:
   receiving and recording the electric signal from the photoacoustic wave sensor;
   estimating timing of occurrence of noise in the electric signal, from a thickness of the arrangement spacer; and
   removing the electric signal at the timing estimated, from contents recorded by the receiving and recording of the electric signal.

* * * * *